US012653470B2

(12) United States Patent
Zhan et al.

(10) Patent No.: US 12,653,470 B2
(45) Date of Patent: Jun. 16, 2026

(54) PIXEL-BASED NUMBER OF ENERGY BIN MATERIAL DECOMPOSITION FOR REDUCING DATA REQUIREMENTS

(71) Applicant: CANON KABUSHIKI KAISHA, Tokyo (JP)

(72) Inventors: Xiaohui Zhan, Vernon Hills, IL (US); Ilmar Hein, Vernon Hills, IL (US); Ruoqiao Zhang, Vernon Hills, IL (US)

(73) Assignee: CANON KABUSHIKI KAISHA, Tokyo (JP)

( * ) Notice: Subject to any disclaimer, the term of this patent is extended or adjusted under 35 U.S.C. 154(b) by 192 days.

(21) Appl. No.: 18/490,568

(22) Filed: Oct. 19, 2023

(65) Prior Publication Data

US 2025/0127467 A1     Apr. 24, 2025

(51) Int. Cl.
    *A61B 6/42*        (2024.01)
    *G06T 12/20*       (2026.01)
(52) U.S. Cl.
    CPC ............ *A61B 6/4241* (2013.01); *G06T 12/20* (2026.01); *G06T 2211/421* (2013.01)
(58) Field of Classification Search
    CPC ....... A61B 6/4241; A61B 6/032; A61B 6/482; A61B 6/5205; G06T 11/006
    See application file for complete search history.

(56) References Cited

U.S. PATENT DOCUMENTS

| | | | |
|---|---|---|---|
| 8,897,531 B2 * | 11/2014 | Flohr | ..................... A61B 6/503 |
| | | | 382/131 |
| 10,034,652 B2 | 7/2018 | Cho et al. | |
| 10,905,388 B2 | 2/2021 | Kojima et al. | |
| 2016/0054453 A1 * | 2/2016 | Moriyasu | ............. A61B 6/4035 |
| | | | 378/19 |

(Continued)

OTHER PUBLICATIONS

Radin A. Nasirudin, et al., A comparison of material decomposition techniques for dual-energy CT colonography, Medical Imaging 2015: Physics of Medical Imaging, Proc. of SPIE vol. 9412, 94124F • © 2015 SPIE • CCC code: 1605-7422/15/$18 • doi: 10.1117/12. 2081982, 6 pgs.

(Continued)

*Primary Examiner* — Casey Bryant
(74) *Attorney, Agent, or Firm* — Oblon, McClelland, Maier & Neustadt, L.L.P.

(57)        ABSTRACT

A photon-counting imaging system is provided. The system includes a photon-counting detector and processing circuitry. The detector acquires, from an imaging object, projection data for a plurality of projection views. The detector has a plurality of detector pixels that are arranged in both a channel direction and a segment direction on a surface of the detector. The processing circuitry obtains the projection data acquired by the detector. The projection data includes first and second projection data. The processing circuitry processes, with a first energy bin setting, the first projection data, the first energy bin setting having m energy bins, and processes, with a second energy bin setting, the second (Continued)

500

S510    Obtain the projection data detected from the imaging object by the detector S520    Using the first energy bin setting, process the first projection data acquired by the detector pixels in the first detector area S530    Using the second energy bin setting, process the second projection data acquired by the detector pixels in the second detector area S540    Generate a material decomposition image of the imaging object, based on the processed first projection data and the processed second projection data projection data, the second energy bin setting having n energy bins, where n>m. The processing circuitry generates, based on the processed first projection data and the processed second projection data, a material decomposition image of the imaging object.

20 Claims, 13 Drawing Sheets

(56) References Cited

U.S. PATENT DOCUMENTS

| | | |
|---|---|---|
| 2016/0058404 A1 | 3/2016 | Nitta et al. |
| 2016/0206255 A1 | 7/2016 | Gagnon et al. |
| 2021/0106292 A1 | 4/2021 | Kojima et al. |
| 2021/0404975 A1 | 12/2021 | Zhan et al. |
| 2022/0313203 A1 | 10/2022 | Zhan et al. |
| 2022/0395243 A1 | 12/2022 | La Riviere et al. |

OTHER PUBLICATIONS

Xiaohui Zhan, et al, Phantom imaging evaluations of a prototype, National Cancer Center East, ECR 2022, Building Bridges, July 13-17, Vienna & Online, 20 pgs.

* cited by examiner

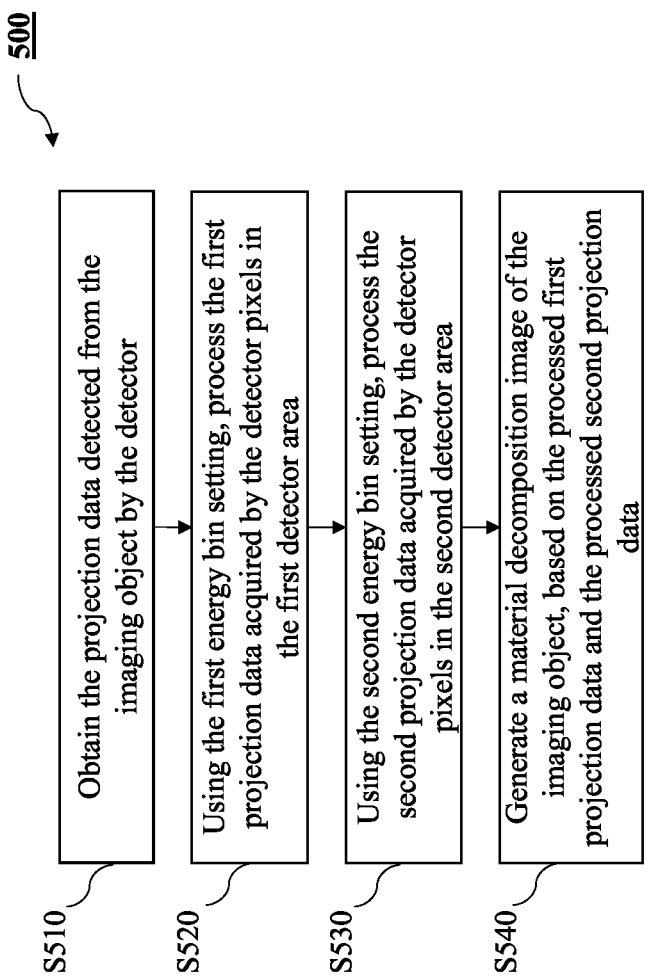

500

S510 — Obtain the projection data detected from the imaging object by the detector S520 — Using the first energy bin setting, process the first projection data acquired by the detector pixels in the first detector area S530 — Using the second energy bin setting, process the second projection data acquired by the detector pixels in the second detector area S540 — Generate a material decomposition image of the imaging object, based on the processed first projection data and the processed second projection data

FIG. 5

$N_{Ch}$          Number of detector channels
$FOV_{Hi}$        High IQ FOV diameter
$N_{ChHi}$        Number of channels for high IQ $FOV_{Hi}$
$N_{ChLow}$       Number of channels for lower IQ periphery
$SOD$             Source Isocenter distance
$FanAng$          Fan angle $$N_{ChHi} = \frac{2N_{Ch}}{FanAng} \cdot sin^{-1}\left(\frac{FOV_{Hi}}{2SOD}\right)$$

$$N_{ChLow} = \frac{N_{Ch} - N_{ChHi}}{2}$$

PIXEL-BASED NUMBER OF ENERGY BIN MATERIAL DECOMPOSITION FOR REDUCING DATA REQUIREMENTS

BACKGROUND

Field

The disclosure relates to X-ray imaging systems based on a photon-counting detector.

Description of the Related Art

Material decomposition is a valuable technique utilized in computed tomography (CT) for distinguishing and quantifying materials. It exploits the energy dependence of the linear attenuation coefficient of different materials and requires at least two energy bins. Dual-energy CT systems commonly incorporate material decomposition as a function, which can be performed on an image or projection basis.

Typically, a photon-counting CT (PCCT) system has more than two energy bins. Thus, PCCT systems are well suited for material decomposition. Additionally, projection-based material decomposition can play a crucial role in the calibration process of PCCT systems.

However, the amount of data needed increases linearly with the number of energy bins used. To achieve high image quality, a larger number of energy bins are necessary, which results in higher demands for data memory or storage and data transfer rates.

It is desirable to address the above issue and other challenges associated with the current material decomposition approaches.

SUMMARY

Disclosed is a photon-counting imaging system including a photon-counting detector and processing circuitry. The photon-counting detector acquires, from an imaging object, projection data for a plurality of projection views. The photon-counting detector has a plurality of detector pixels that are arranged in both a channel direction and a segment direction on a surface of the photon-counting detector. The processing circuitry obtains the projection data acquired by the photon-counting detector. The projection data includes first projection data and second projection data. The processing circuitry processes, with a first energy bin setting, the first projection data, the first energy bin setting indicating use of m energy bins, and processes, with a second energy bin setting, the second projection data, the second energy bin setting indicating use of n energy bins, where n>m. The processing circuitry generates, based on the processed first projection data and the processed second projection data, a material decomposition image of the imaging object.

Also disclosed is a method for performing pixel-based energy bin number modulation in a photon-counting imaging system. The photon-counting imaging system includes a photon-counting detector that acquires, from an imaging object, projection data for a plurality of projection views. The photon-counting detector has a plurality of detector pixels that are arranged in both a channel direction and a segment direction on a surface of the photon-counting detector. The method includes obtaining the projection data acquired by the photon-counting detector, the projection data including first projection data and second projection data, processing, with a first energy bin setting, the first projection data, the first energy bin setting indicating use of m energy bins, processing, with a second energy bin setting, the second projection data, the second energy bin setting indicating use of n energy bins, where n>m, and generating, based on the processed first projection data and the processed second projection data, a material decomposition image of the imaging object.

Also disclosed is a non-transitory computer-readable medium storing a program that, when executed by processing circuitry, causes the processing circuitry to execute a method for performing pixel-based energy bin number modulation in a photon-counting imaging system. The photon-counting imaging system includes a photon-counting detector that acquires, from an imaging object, projection data for a plurality of projection views. The photon-counting detector has a plurality of detector pixels that are arranged in both a channel direction and a segment direction on a surface of the photon-counting detector. The method includes obtaining the projection data acquired by the photon-counting detector, the projection data including first projection data and second projection data, processing, with a first energy bin setting, the first projection data, the first energy bin setting indicating use of m energy bins, processing, with a second energy bin setting, the second projection data, the second energy bin setting indicating use of n energy bins, where n>m, and generating, based on the processed first projection data and the processed second projection data, a material decomposition image of the imaging object.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the disclosure and embodiments, the reader is directed to the Detailed Description section and corresponding figures of the present disclosure as further discussed below.

BRIEF DESCRIPTION OF THE DRAWINGS

The application will be better understood in light of the description which is given in a non-limiting manner, accompanied by the attached drawings in which:

FIG. 5 shows a flow chart of a material decomposition performing procedure 500 that implements pixel-based energy bin numbers, according to embodiments of the disclosure;

DETAILED DESCRIPTION OF THE PREFERRED EMBODIMENTS

The following disclosure provides many different embodiments, or examples, for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present disclosure can be embodied and viewed in many different ways.

Furthermore, as used herein, the words "a," "an," and the like generally carry a meaning of "one or more," unless stated otherwise.

This disclosure relates to pixel-based energy bin number modulation used in a photon-counting CT (PCCT) scanning system, said scanning system including one or more X-ray tubes that emit X-ray radiation, and an array of detector pixels for receiving the X-ray radiation propagating through a field of view (FOV) of the scanning system. The array of detector pixels is arranged in lines in both the channel direction and the segment direction on the surface of the detector. The energy bin number modulation scheme can be applied to the material decomposition mode of the PCCT scanning system.

PCCT systems use a direct conversion photon-counting detector (PCD) to resolve the energy of the individual incoming photons and generate measurement of multiple energy bin counts for each integration period. The transmission forward model for this energy resolving PCD can be formulated as below:

$$N_b(l_{1,...,M}) = N_0 \times \int dE w(E) S_b(E) \exp\left(- \sum_m \mu_m l_m\right),$$

where $S_b(E)$ represents the bin response function defined as $$S_b(E) = \int_{E_{bL}}^{E_{bH}} dE' R(E, E'), R(E, E')$$

is the detector response function, $E_{bL}$ and $E_{bH}$ are the low and high energy thresholds of each counting bin, No is the total flux from an air scan, $\mu_m$ and $l_m$ are the m-th basis material linear attenuation coefficient and pathlength, and w(E) is the normalized incident X-ray spectrum.

Figure 1:
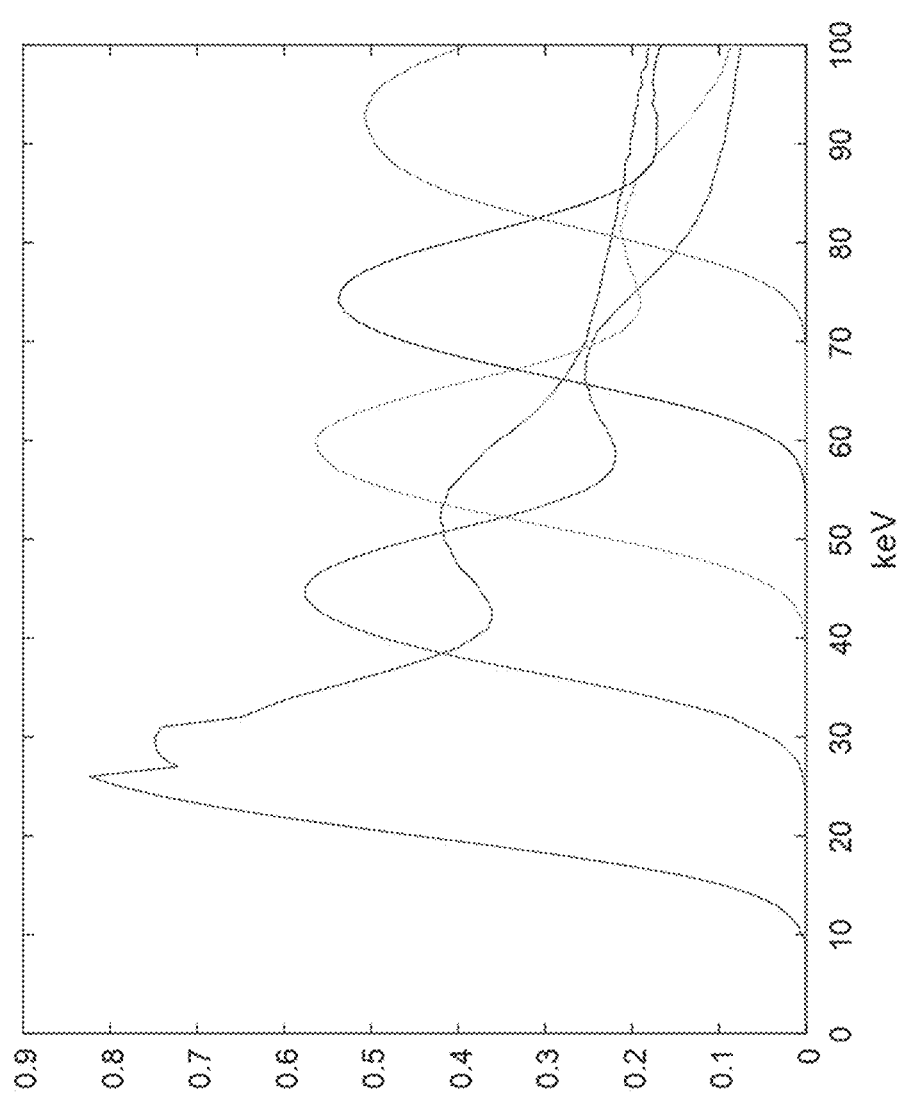
FIG. 1 shows an exemplary bin response function S; (E) for a photon-counting detector (PCD), with each curve standing for a response function corresponding to an energy bin.

For PCCT systems, more than two energy bins are available, and these energy bins can be used in the projection-based decomposition. FIG. 1 shows an exemplary bin response function $S_b(E)$ for a PCD with five energy bins. Each curve in FIG. 1 corresponds to a response function associated with one of the five energy bins.

Figure 2:
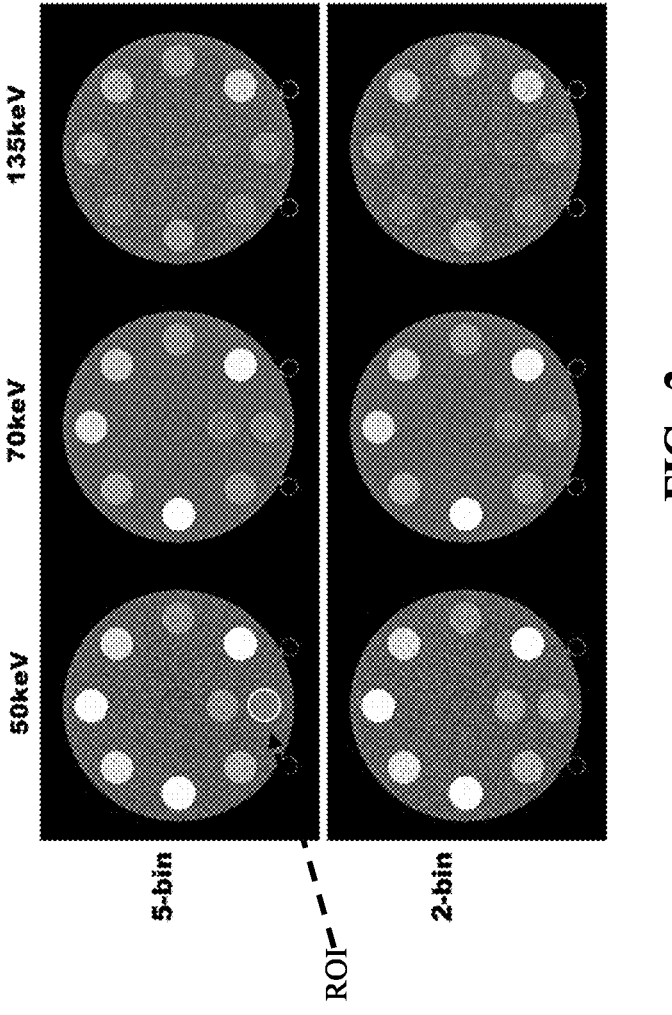
FIG. 2 shows virtual monochromatic energy reconstructions at 50, 70, and 135 keV for photon-counting CT (PCCT) systems using five energy bins and two energy bins, respectively.

FIG. 2 illustrates a comparison of virtual monochromatic energy reconstructions at 50, 70, and 135 keV for PCCT systems using five energy bins and two energy bins. As observed from FIG. 2, the image quality of PCCT material decomposition improves when more energy bins are used.

Moreover, Table 1 below presents the measured noise standard deviation (SD) within the arrowed region of interest (ROI) in FIG. 2. This table compares the noise SD measured in virtual monochromatic energy reconstructions for 5-bin and 2-bin decomposition. The resulting noise in the reconstructions at 50, 70, and 135 keV is 24.5%, 20.5%, and 22.0% higher, respectively, when only two energy bins are used instead of five energy bins.

TABLE 1

| Measured noise SD in the arrowed ROI for 5-bin and 2-bin decomposition | | | |
| --- | --- | --- | --- |
| Number of Energy Bins used in Decomp ($N_{Ebins}$) | 50 keV Noise SD | 70 keV Noise SD | 135 keV Noise SD |
| 5-bin (30/45/55/65/80) | 33.1 | 11.2 | 28.0 |
| 2-in (30/65) | 41.2 | 13.5 | 34.2 |
| Noise increased in 2-bin decomp | 24.5% | 20.5% | 22.0% |

Figure 3:
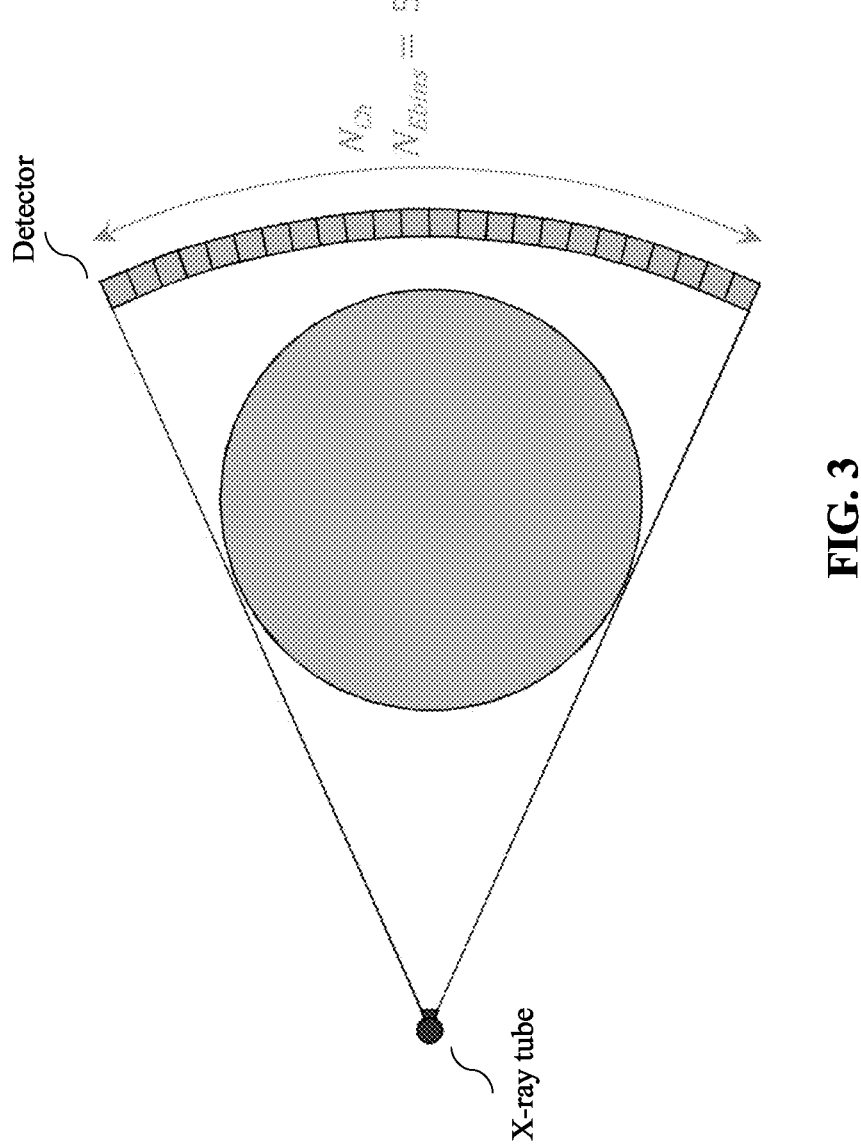
FIG. 3 shows a scenario where a single value of the energy bin number $N_{Ebins}$ is adopted in the channel direction for the entire projection view.

Projection-based material decomposition is performed at the level of individual detector pixels. Typically, only a single value of $N_{EBins}$ per pixel is used in the material decomposition process, and this value is uniformly applied to all pixels in one projection view. FIG. 3 shows this commonly adopted approach, where a single value of $N_{Ebins}$, e.g., 5, is used in the channel direction across the entire projection view. The segment direction is not depicted in FIG. 3.

It is desirable to achieve the highest possible image quality, which implies using the maximum number of energy bins. However, utilizing the maximum amount of energy bins leads to the most amount of data, demanding high data storage and fast data transfer rates, which requires increased memory or disk space and slows down processing time.

In general, the amount of data required in the material decomposition process increases linearly with $N_{EBins}$, and the total number of data values, $N_{values}$, can be calculated by:

$$N_{values} = N_{ch} \cdot N_{EBins} \cdot N_{Seg},$$

where $N_{ch}$ and $N_{Seg}$ denote the number of detector channels and the number of the detector segments, respectively. In comparison to a PCCT system with two energy bins, the data required for a 5-bin system is 2.5 times larger, for example. Thus, the challenge is to retain the highest image quality while reducing the amount of data required by the maximum amount of energy bins.

Figure 4:
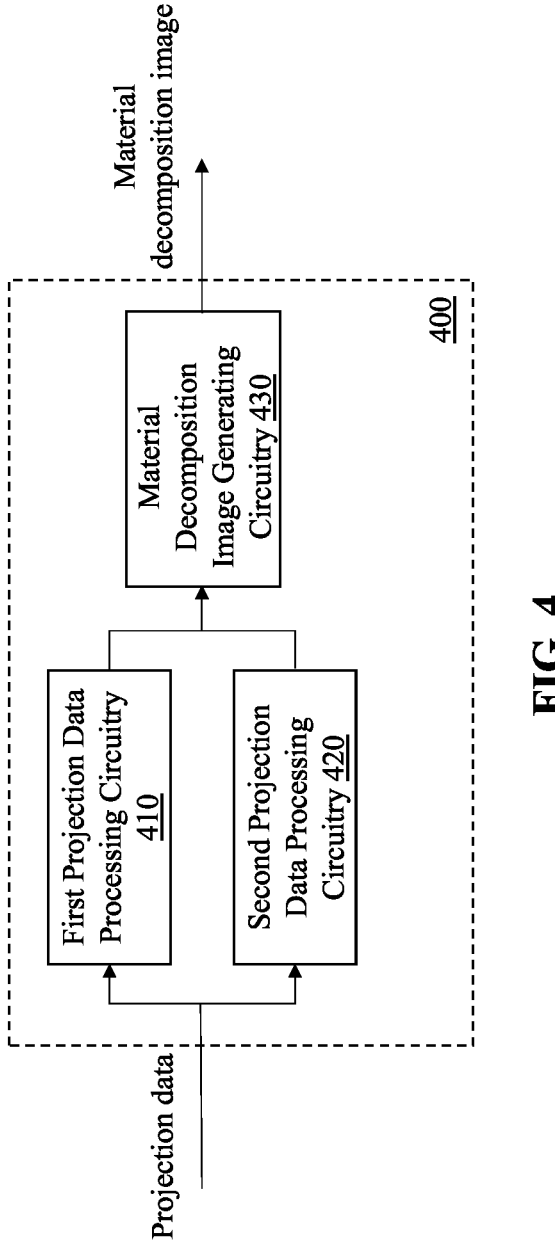
FIG. 4 shows a block diagram of a material decomposition performing apparatus 400 that implements pixel-based energy bin numbers, according to embodiments of the disclosure.

FIG. 4 illustrates a block diagram of a material decomposition performing apparatus 400 according to embodiments of the disclosure. The apparatus 400 includes first projection data processing circuitry 410, second projection data processing circuitry 420, and material decomposition image generating circuitry 430.

The first projection data processing circuitry 410 and the second projection data processing circuitry 420 receive projection data acquired from the imaging object by the PCD. Since not all projection data originates from the region of interest (corresponding to the FOV part where the image quality requirement is high) within the imaging object, the projection data can be processed differently based on the positions of the reconstructed image pixels. This allows for the utilization of a larger number of energy bins to process the projection data from the region of interest while using a smaller number of energy bins for processing the projection data from other regions (e.g., the FOV part where the image quality requirement is lower). By doing so, it is possible to reduce the amount of data without compromising the quality of the reconstructed image.

Specifically, the first projection data processing circuitry 410 can process the projection data from a subset of detector pixels using a first energy bin setting with a smaller number of energy bins. In contrast, the second projection data processing circuitry 420 can process the projection data from another subset of detector pixels using a second energy bin setting with a larger number of energy bins.

For example, the second energy bin setting can use all of the five energy bins that are determined by a set of predefined energy thresholds in the PCCT system, and the first energy bin setting can use fewer energy bins, e.g., two energy bins. The reduced number of energy bins can be obtained through a recombination of the original five energy bins.

For instance, in one recombination scenario, Bin 1 and Bin 2 can be merged to form an energy bin, while Bin 3, Bin 4, and Bin 5 can be merged to create another energy bin. Alternatively, in a different recombination scenario, Bins 1, 2, and 4 can be combined as one energy bin, and Bins 3 and 5 can be combined as another one. These exemplary scenarios are not restrictive, as there are numerous other possible recombination scenarios available.

The material decomposition image generating circuitry 430 receives data processed by the first projection data processing circuitry 410 and the second projection data processing circuitry 420, and generates a material decomposition image of the imaging object.

FIG. 5 shows a flow chart of a material decomposition performing procedure 500 according to embodiments of the disclosure. The procedure 500 starts with step S510, where the projection data acquired from the imaging object by the PCD is obtained.

In step S520, the first energy bin setting with fewer energy bins can be used to process the first projection data acquired by the detector pixels within a first detector area.

In step S530, the second energy bin setting with more energy bins can be used to process the second projection data acquired by the detector pixels within a second detector area.

Finally, in step S540, a material decomposition image of the imaging object is generated based on the processed first projection data and the processed second projection data.

Figure 6:
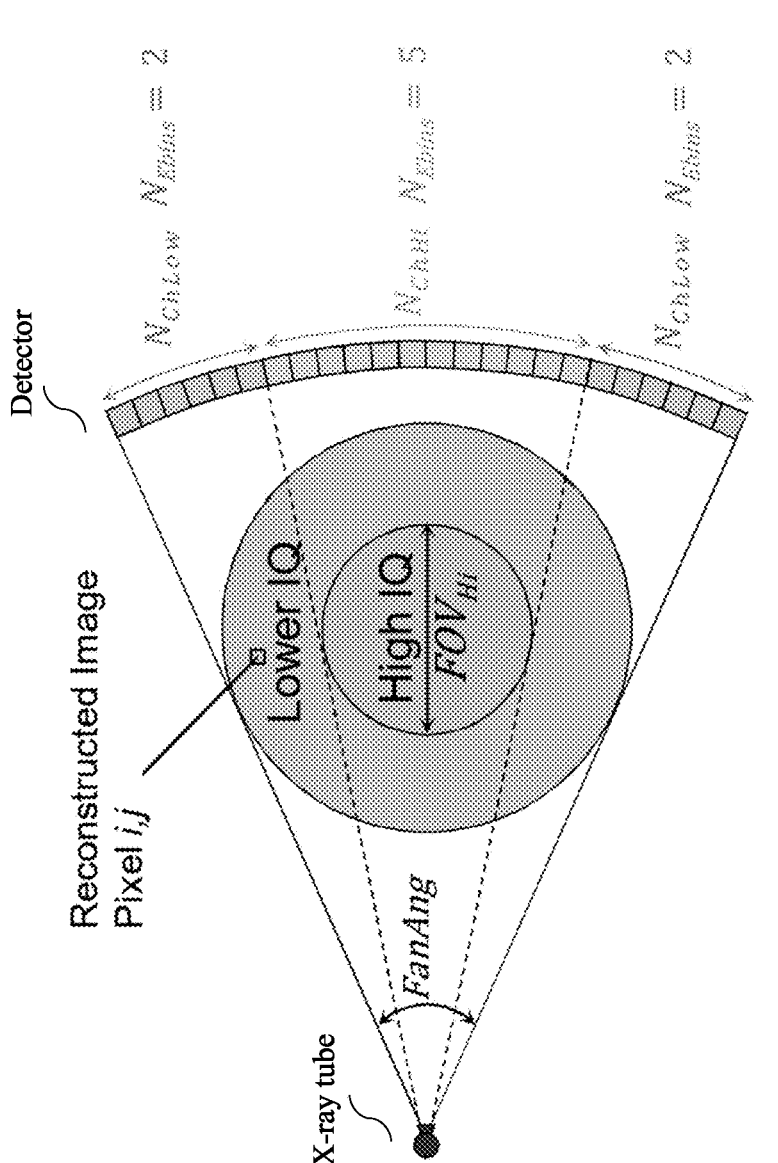
FIG. 6 shows an exemplary approach where a higher value of $N_{Ebins}$ is used for the central region of the detector in the channel direction while a lower value of $N_{Ebins}$ is used for the peripheral regions of the detector in the channel direction, in accordance with one embodiment of the disclosure.

FIG. 6 shows an exemplary approach where different pixel areas on the detector surface utilize varying values of $N_{Ebins}$, in accordance with one embodiment of the disclosure. In FIG. 6, a larger value (e.g., 5) of $N_{Ebins}$ is used for the central part of the detector in the channel direction, where high image quality is required. Conversely, a smaller value (e.g., 2) of $N_{Ebins}$ is used for the two peripheral portions of the detector in the channel direction, where lower image quality is acceptable.

The total amount of the required data, $N_{Values}$, can be calculated as follows:

$$N_{Values} = (N_{ChLow} \cdot N_{EBinsLow} + N_{ChHi} \cdot N_{EBinsHi}) \cdot N_{seg}$$

where $N_{ChLow}$ denotes the number of the channels with the lower energy bin number $N_{EbinsLow}$, $N_{ChHi}$ represents the number of the channels with the higher energy bin number $N_{EbinsHi}$, and $N_{seg}$ denotes the number of the detector segments.

In the example of FIG. 6, for any reconstructed image pixel i,j (represented by a square in FIG. 6), $N_{Ebins}$ remains the same for all projection views. By using a higher number of energy bins to process projection data detected by the central region of the detector (corresponding to the high image quality (IQ) center of the FOV), and a lower number of energy bins to process projection data from detected by the remaining detector regions (corresponding to the lower IQ periphery of the FOV), it is possible to maintain image quality while reducing overall data requirements.

The high $N_{EBins}$ range on the detector can be determined based on the size of the high IQ center of the FOV. Let $N_{ch}$ denote the total number of the detector channels, $FOV_{Hi}$ represent the diameter of the high IQ center, SOD denote the source-isocenter distance, and FanAng denote the fan angle. The number of the detector channels with a higher $N_{Ebins}$ and the number of the detector channels with the lower $N_{Ebins}$ can be calculated as follows:

$$N_{ChHi} = \frac{2N_{Ch}}{FanAng} \cdot \sin^{-1}\left(\frac{FOV_{Hi}}{2SOD}\right)$$

$$N_{ChLow} = \frac{N_{Ch} - N_{ChHi}}{2}$$

In the embodiment shown in FIG. 6, $N_{Ebins}$ are partitioned in the channel direction. However, in an alternative approach, the partitioning can be performed in the segment direction instead of the channel direction. Furthermore, these two embodiments can be combined, allowing for partitioning in both the segment and channel directions simultaneously, as exemplarily shown in FIG. 7.

Figure 7:
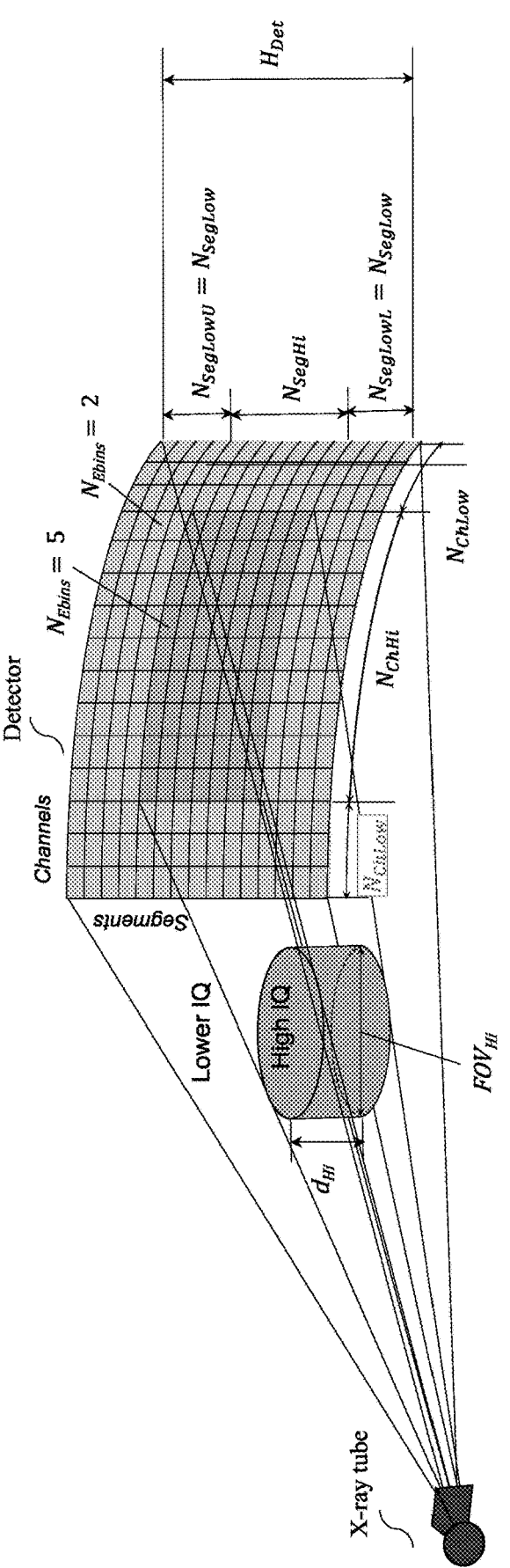
FIG. 7 shows an exemplary approach where a higher value of $N_{Ebins}$ is used for the inner region of the detector in both the channel direction and the channel direction while a lower value of $N_{Ebins}$ is used for the outer region of the detector in both the channel direction and the channel direction, in accordance with one embodiment of the disclosure.

FIG. 7 illustrates an exemplary approach where a higher value of $N_{Ebins}$ is used for the inner region of the detector in both the channel direction and the channel direction while a lower value of $N_{Ebins}$ is used for the outer region of the detector in both the channel direction and the channel direction, in accordance with one embodiment of the disclosure.

In this case, the total amount of the required data, $N_{values}$, can be calculated as:

$$N_{Values} = N_{ChLow} \cdot N_{SegLow} \cdot N_{EBinsLow} + N_{ChHi} \cdot N_{SegHi} \cdot N_{EBinsHi}$$

where $N_{ChLow}$ and $N_{SegLow}$ denotes the number of channels and segments (corresponding to the low IQ peripheral volume of the imaging object) with a lower energy bin number $N_{EBinsLow}$, and $N_{ChHi}$ and $N_{SegHi}$ denotes the number of channels and segments (corresponding to the high IQ central volume of the imaging object) with a higher energy bin number $N_{EBinsHi}$.

In this embodiment, the high IQ imaging volume corresponds to the center of the detector. Let $d_{Hi}$ denote the high IQ FOV axial height, $H_{Det}$ denote the physical height of the detector, SDD denote the source-detector distance, and $N_{seg}$ denotes the total number of the detector segments. Given $N_{SegLowU}=N_{SegLowL}=N_{SegLow}$, the $N_{SegHi}$ and $N_{SegLow}$ can be calculated as follows:

$$N_{SegHi} = \frac{N_{Seg} \cdot d_{Hi} \cdot SDD}{H_{Det} \cdot \left(SOD - \frac{FOV_{Hi}}{2}\right)}$$

$$N_{SegLow} = \frac{N_{Seg} - N_{SegHi}}{2}$$

One skilled in the art can recognize that in alternate embodiments, $d_{Hi}$ does not have to be centered with respect to the height of the detector, and $N_{SegLowU}$ can be different from $N_{SegLowL}$.

Figure 8:
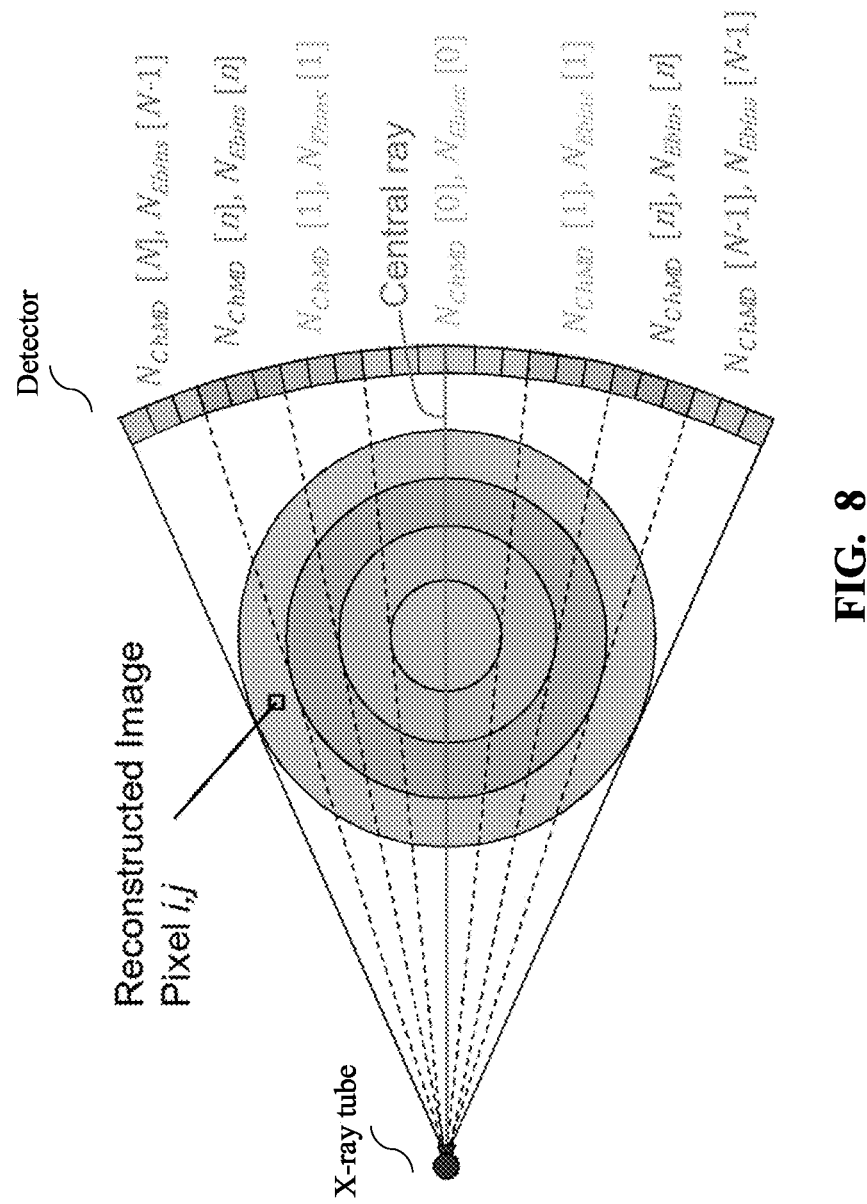
FIG. 8 shows an exemplary approach where more than two values of $N_{Ebins}$ are incorporated, without overlapping in $N_{Ebins}$ values between adjacent $N_{ChMD}$ ranges, in accordance with one embodiment of the disclosure.

The previous FIGS. 6-7 illustrate scenarios where two values of $N_{Ebins}$ are incorporated. In a more generalized case, N values of $N_{Ebins}$ can be used to provide a smoother transition of image quality from the center towards the edges of the detector. FIG. 8 shows an exemplary approach where more than two values of $N_{Ebins}$ are implemented in the channel direction, in accordance with one embodiment of the disclosure.

The total amount of the required data, $N_{Values}$, can be calculated as follows:

$$N^{Values} = N_{Seg} \cdot \sum_{n=0}^{N-1} N_{ChMD}[n] \cdot N_{EBins}[n]$$

where $N_{Seg}$ denotes the number of detector segments, $N_{ChMD}[n]$ denotes the number of the channels with the energy bin number $N_{Ebins}[n]$, and n ranges from 0 to N−1.

In this embodiment, for n=0, 1, . . . , N−1, $N_{Ebins}$ [n] and $N_{ChMD}$ [n] are symmetric about the central X-ray. For any reconstructed image pixel i,j (represented by the square in FIG. 8), $N_{Ebins}$ remains the same for all projection views. Although FIG. 8 illustrates the case for the channel direction, the same concept can be applied to the segment direction as well.

In FIG. 8, each combination {$N_{ChMD}$ [n], $N_{Ebins}$ [n]} sweeps out an annulus over a 360° range of views, with no overlapping or mixing in $N_{Ebins}$ values between adjacent $N_{ChMD}$ ranges. In an alternate embodiment, for the purposes of providing an even smoother transition in image quality, there can be overlapping between {$N_{ChMD}$ [n], $N_{Ebins}$ [n]} and {$N_{ChMD}$ [n+1], $N_{Ebins}$ [n+1]}, as described below with reference to FIG. 9.

Figure 9:
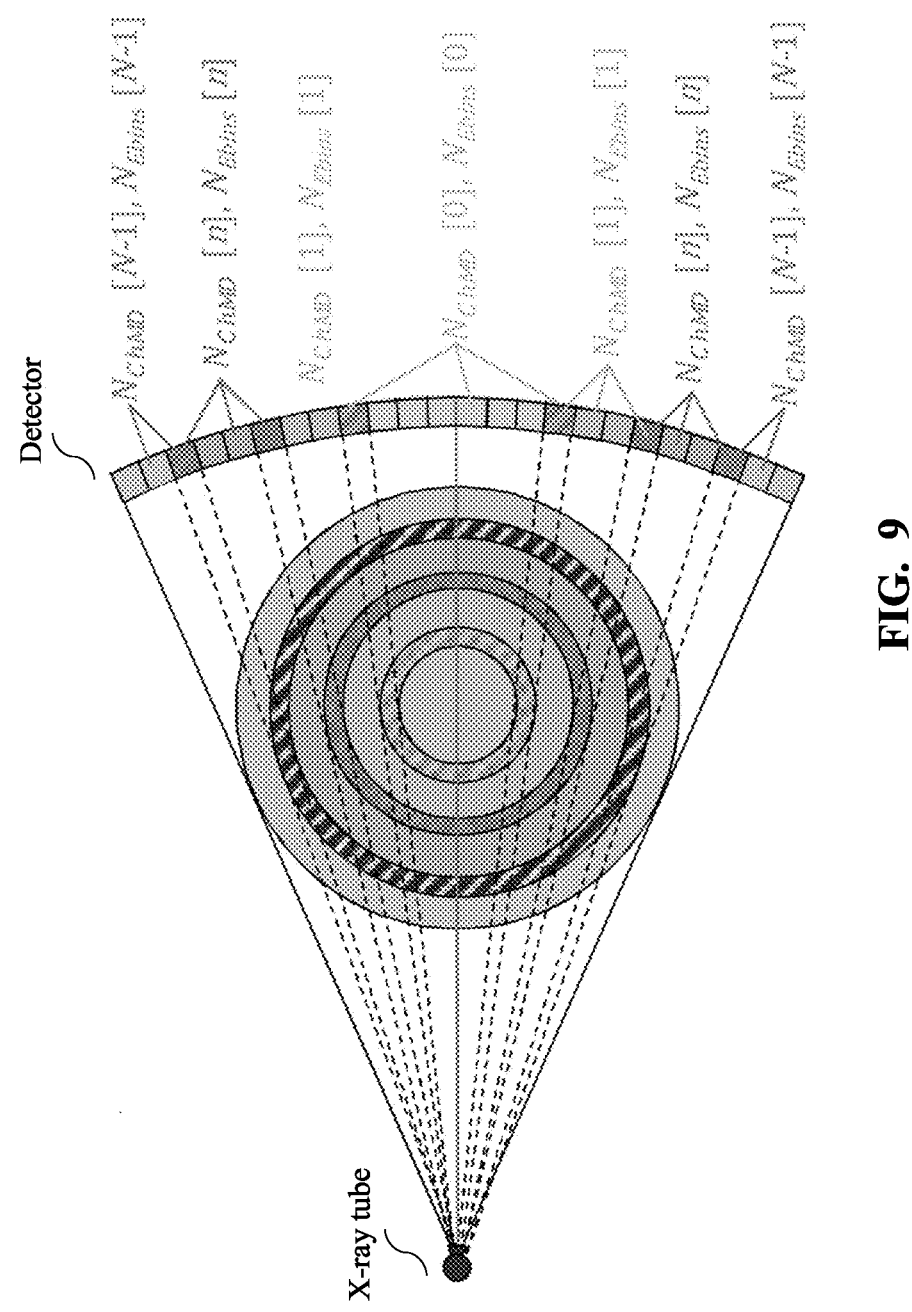
FIG. 9 shows an exemplary approach where more than two values of $N_{Ebins}$ are incorporated, with overlapping in $N_{Ebins}$ values between adjacent $N_{ChMD}$ ranges, in accordance with one embodiment of the disclosure.

FIG. 9 shows an exemplary approach where more than two values of $N_{Ebins}$ are incorporated, with overlapping in $N_{Ebins}$ values between adjacent $N_{ChMD}$ ranges, in accordance with one embodiment of the disclosure. On the detector, the solid areas represent channels where only $N_{Ebins}$ [n] is used; the hatched areas represent channels where both $N_{Ebins}$ [n] and $N_{Ebins}$ [n+1] are used, with n ranging from 0 to N−1. Thus, reconstructed image pixels i,j in the overlapping regions can have contributions from two values of $N_{Ebins}$. For example, the overlapping region can be reconstructed with one value of $N_{Ebins}$, and also reconstructed with another value of $N_{Ebins}$, and then averaged.

Similar to the embodiment shown in FIG. 8, for n=0, 1, . . . , N−1, $N_{Ebins}$ [n] and $N_{ChMD}$ [n] are symmetric with respect to the central X-ray. Although FIG. 9 illustrates the case for the channel direction, the same concepts can be applied to the segment direction as well.

Note that the pixel-based energy bin number modulation described in this disclosure is not limited to symmetric portioning of $N_{Ebins}$ illustrated in FIGS. 6-9. In alternative embodiments, it is possible to implement asymmetric partitioning of $N_{Ebins}$.

Figures 10A, 10B:
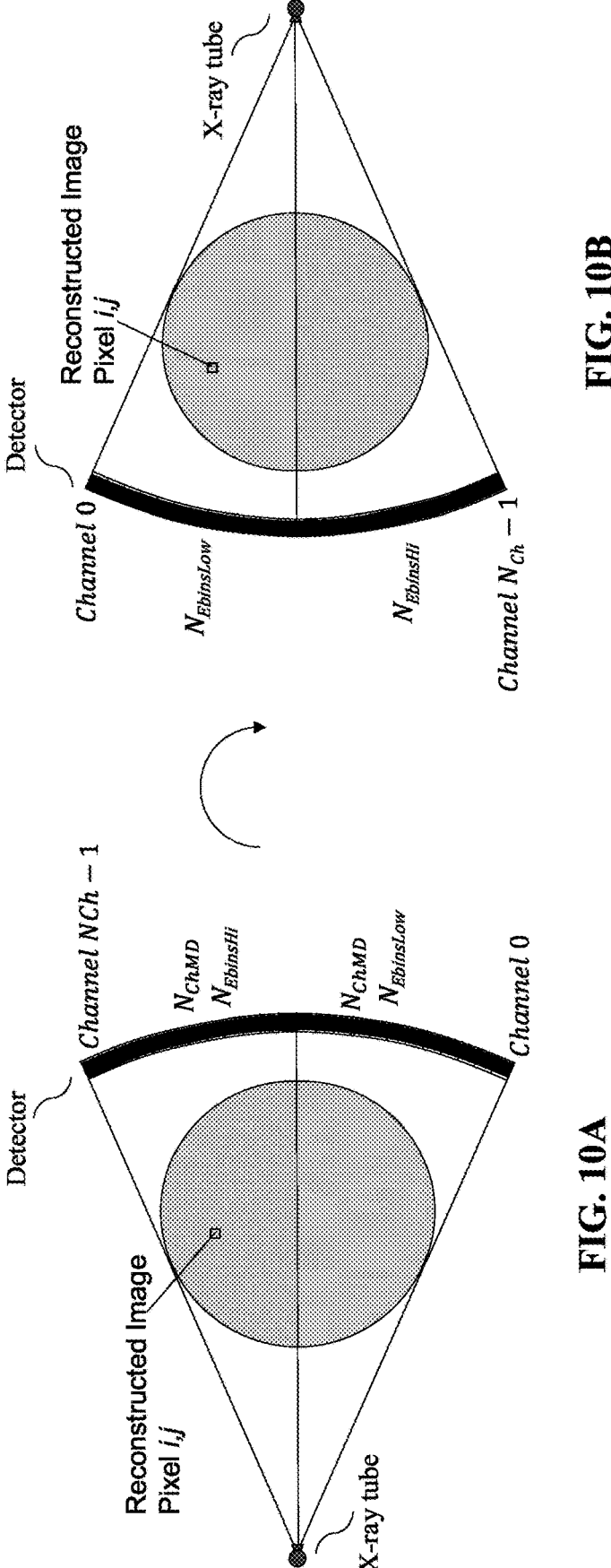
FIGS. 10A-10B show an exemplary approach with asymmetric partitioning of $N_{Ebins}$ in the channel direction for projection views at 0 and 180 degrees, respectively, in accordance with one embodiment of the disclosure.

FIGS. 10A-10B show an exemplary approach with asymmetric partitioning of two values of $N_{Ebins}$ in the channel direction for projection views at 0 and 180 degrees, respectively, in accordance with one embodiment of the disclosure.

As illustrated in FIGS. 10A and 10B, for any given pixel i,j in the reconstructed image, $N_{Ebins}$ can be different depending on the view angle. For example, in the 0-degree projection view (FIG. 10A), a higher value, $N_{EbinsHi}$, is applied to the top half of the detector, while a lower value, $N_{EbinsLow}$, is applied to the bottom half. In the 180-degree projection view (FIG. 10B), the lower value, $N_{EbinsLow}$, is applied to the top half of the detector and the higher value, $N_{EbinsHi}$, is applied to the bottom half.

Thus, in this embodiment, the data associated with the two values of $N_{Ebins}$ is effectively "mixed" over 360° of projection views, resulting in a reconstructed image with no distinct high and low IQ regions, but rather an IQ somewhere in between the two.

Figures 11A, 11B:
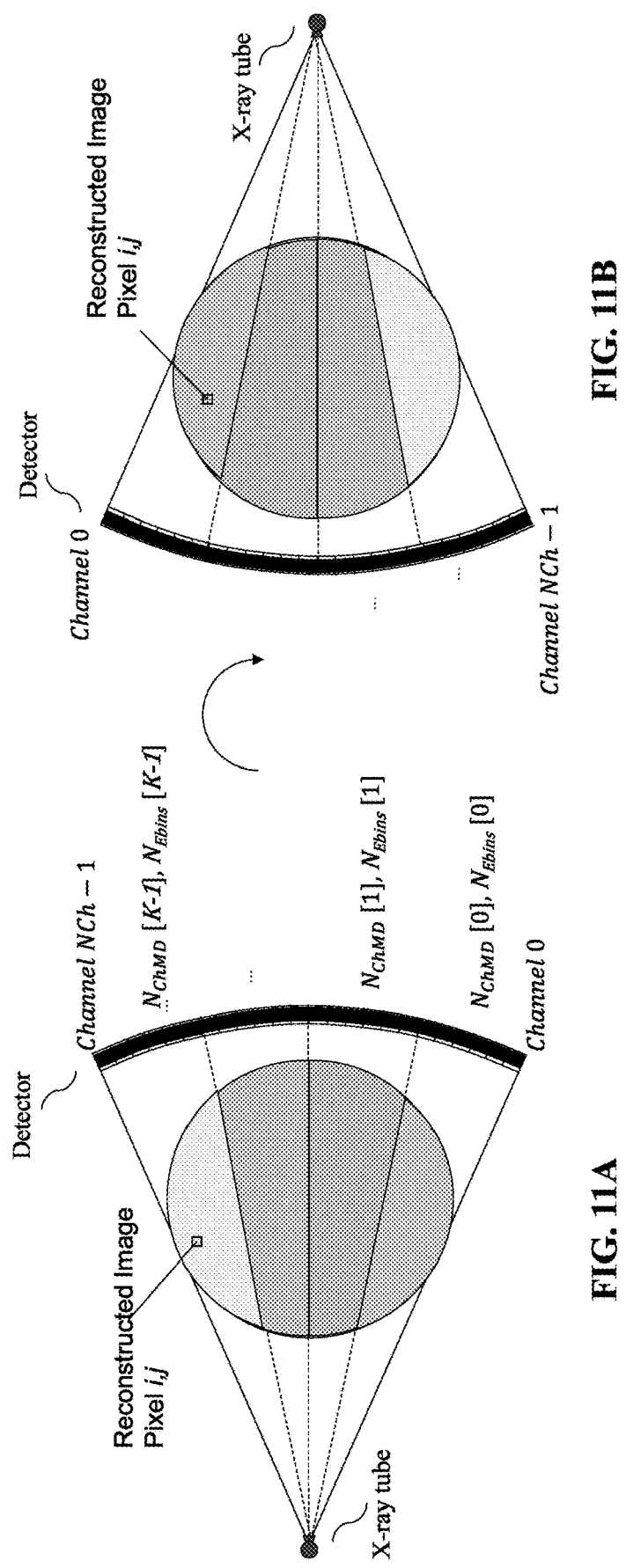
FIGS. 11A-11B show another exemplary approach with asymmetric partitioning of $N_{Ebins}$ in the channel direction for projection views at 0 and 180 degrees, respectively, in accordance with one embodiment of the disclosure.

FIGS. 11A-11B show a more generalized case with asymmetric partitioning of K values $N_{Ebins}$ in the channel direction for projection views at 0 and 180 degrees, respectively, in accordance with one embodiment of the disclosure.

Similar to the embodiment illustrated in FIGS. 10A and 10B, in this embodiment, for any given pixel i,j in the reconstructed image, $N_{Ebins}$ can be different depending on the view angle as well. FIG. 11A shows the projection view at 0 degrees, and FIG. 11B shows the projection view at 180 degrees. Again, the data associated with the K values of $N_{Ebins}$ is effectively mixed over 360° of projection views, resulting in a reconstructed image without distinct high or low IQ regions, but rather an IQ somewhere between the two.

In the previous embodiments, the partitioning and number of $N_{Ebins}$ is implemented within a projection view, and remains constant across different views. In alternative embodiments, the partitioning and number $N_{Ebins}$ can vary from view to view, instead of within one projection view.

For instance, even-numbered projection views can use five energy bins, while odd-numbered projection views can use two energy bins. Other partitioning and energy bin numbers are possible. For example, the projection views can be divided into three or more groups, each group using a different energy bin number.

Figure 12:
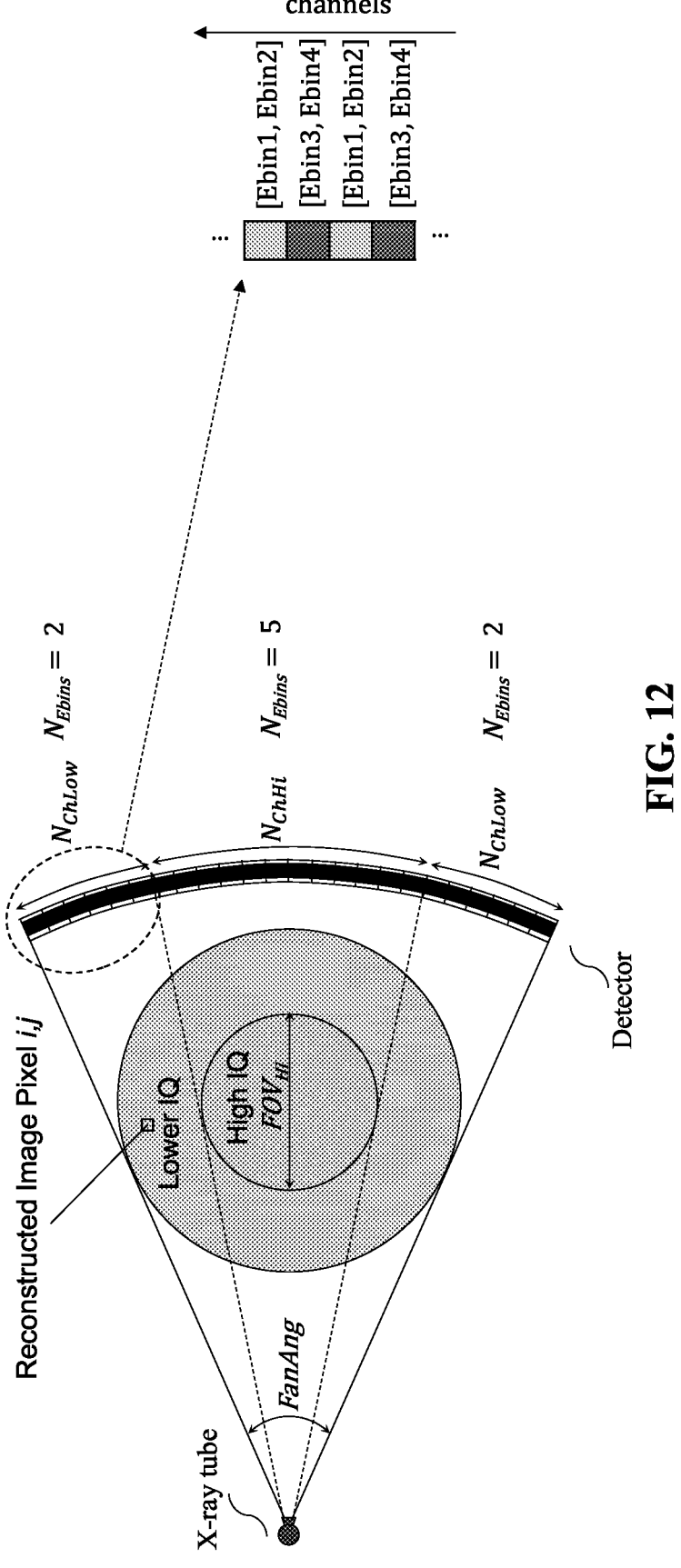
FIG. 12 shows an exemplary approach with different partitioning between adjacent detector channels, in accordance with one embodiment of the disclosure.

Furthermore, for the detector area with a lower energy bin number, the partitioning of $N_{Ebins}$ can be interweaved between adjacent detector channels, segments, and/or projection views. FIG. 12 shows an exemplary approach with different energy partitioning between adjacent detector channels, in accordance with one embodiment of the disclosure.

The zoomed window of FIG. 12 shows that two sorts of partitioning [$E_{bin1}$, $E_{bin2}$] and [$E_{bin3}$, $E_{bin4}$] are applied alternatively in the channel direction. Specifically, in the peripheral portion of the detector, two energy bins, Bins 1 and 2, can be applied to Channels 0, 2, 4, . . . , while two energy bins, Bins 3 and 4, can be applied to Channels 1, 3, 5, . . . , and so on. Here, Bins 1 and 2 can be obtained by recombining the original Bins 1-5 in one way, and Bins 3 and 4 can be obtained by recombining the original Bins 1-5 in another way.

FIG. 12 illustrates two different sorts of partitioning, but three or more sorts of partitioning can also be used. Additionally, although the illustration is presented for the channel level, the same concepts can be applied to the segment level and/or the projection view level as well.

One skilled in the art can recognize that various combinations of the previous embodiments are possible without departing from the scope of this disclosure. For example, although there is no overlapping in $N_{Ebins}$ values between adjacent detector areas in the embodiments shown in FIGS. 10A, 10B, 11A, and 11B, it is possible to apply overlapping $N_{Ebins}$ values in transition zone(s) to achieve smoother image quality. As another example, the asymmetric partitioning within a projection view shown in FIGS. 10A, 10B, 11A, and 11B also can be implemented in the segment direction, or in both the channel and the segment directions.

Figure 13:
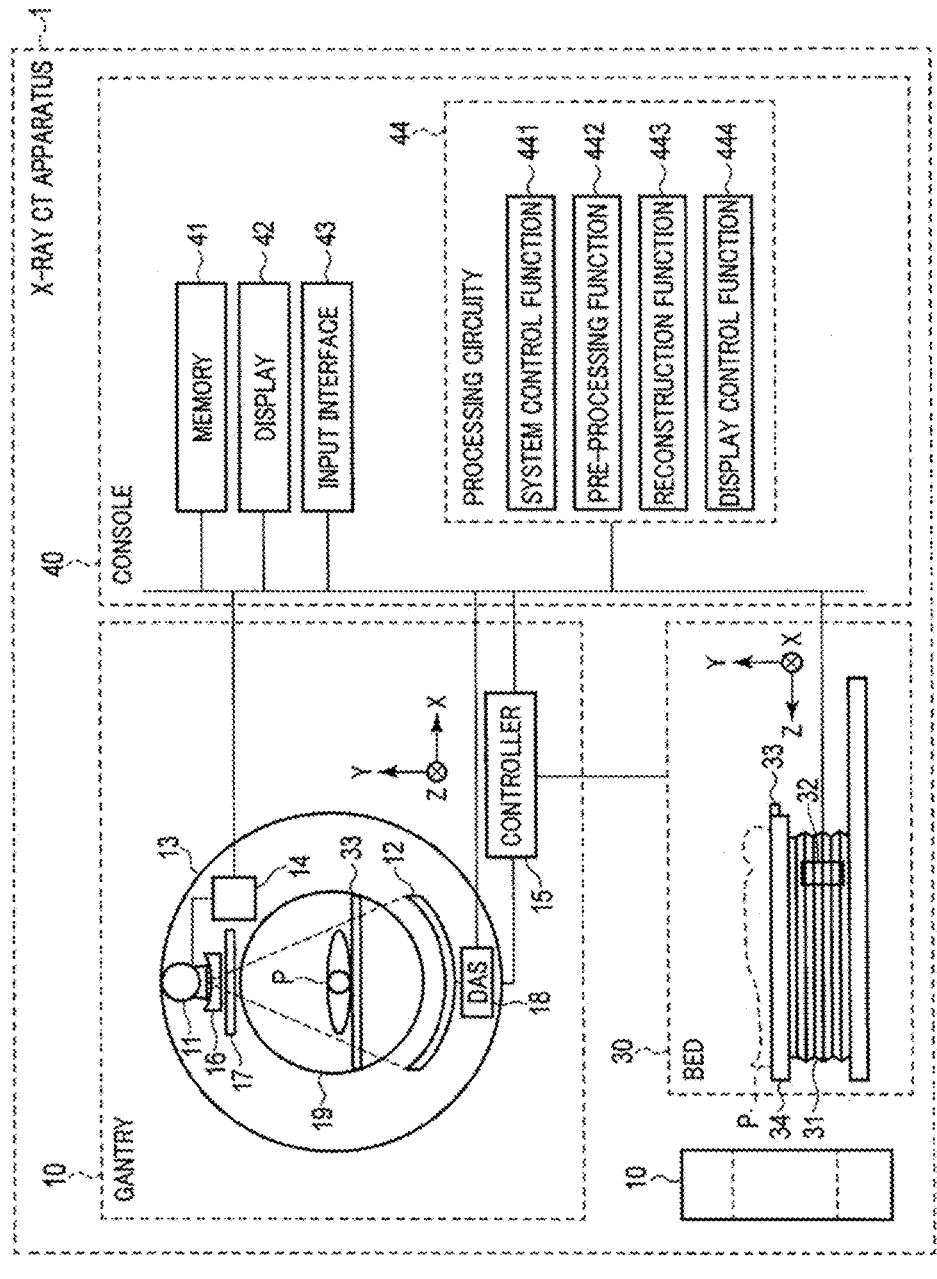
FIG. 13 shows an example of a photon-counting CT scanner system that can incorporate the techniques disclosed herein.

The pixel-based energy bin number modulation can be implemented in a photon-counting CT scanning system as described below with reference to FIG. 13. The X-ray CT apparatus 1 shown in FIG. 13 includes a gantry 10, a bed 30, and a console 40 that implements the processing of a medical imaging processing apparatus. For the sake of explanation, FIG. 13 shows multiple gantries 10.

In the present embodiment, the rotation axis of a rotation frame 13 in the non-tilted state, or the longitudinal direction of a table top 33 of the bed 30, is defined as a "Z-axis direction;" the axial direction orthogonal to the Z-axis direction and horizontal to the floor is defined as an "X-axis direction;" and the axial direction orthogonal to the Z-axis direction and vertical to the floor is defined as a "Y-axis direction."

For example, the gantry 10 and the bed 30 are installed in a CT examination room, and the console 40 is installed in a control room adjacent to the CT examination room. The console 40 is not necessarily installed in the control room. For example, the console 40 can be installed together with the gantry 10 and the bed 30 in the same room. In any case, the gantry 10, the bed 30, and the console 40 are communicably connected to one another by wire or radio.

The gantry 10 is a scanner with a configuration for performing X-ray CT imaging on a subject (or an imaging object) P. The gantry 10 includes an X-ray tube 11, an X-ray detector 12, a rotation frame 13, an X-ray high voltage device 14, a controller 15, a wedge filter 16, a collimator 17, and a data acquisition system (DAS) 18.

The X-ray tube 11 is a vacuum tube that generates X-rays by emitting thermal electrons from the cathode (filament) to the anode (target) in response to application of a high voltage and supply of a filament current from the X-ray high voltage device 14. Specifically, X-rays are generated by the thermal electrons colliding with the target. Examples of the X-ray tube 11 include a rotating anode type X-ray tube that generates X-rays by emitting thermal electrons to the rotating anode. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in the channel direction (the X-axis direction, or the column direction) along an arc having a center at the focus of the X-ray tube 11, for example. The X-ray detector 12 has an array structure in which a plurality of X-ray detection element lines, each including a plurality of X-ray detection elements aligned in the channel direction, are aligned in the segment direction (the Z-axis direction, or the row direction).

Specifically, the X-ray detector 12 can be, for example, a direct conversion type detector including a semiconductor element that converts incident X-rays into an electrical signal. The X-ray detector 12 is an example of the PCD according to the present embodiment, and will also be referred to as a "PCD 12."

The rotation frame 13 supports an X-ray generator and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under the control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter (not shown) to a receiver (not shown) arranged on a non-rotating portion (such as the stationary frame, illustration omitted in FIG. 13) of the gantry, and then transferred to the console 40.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator can be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 can be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The CPU can execute a computer program including a set of computer-readable instructions that perform the functions described herein, and the program is stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor and an operating system known to those skilled in the art. Further, the CPU can be implemented as multiple processors cooperatively working in parallel to perform the instructions.

The controller 15 also has the function of performing operation control of the gantry 10 and the bed 30 in response to an input signal from an input interface 43 to be described later attached to the console 40 or the gantry 10. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction, based on tilt angle information input through the input interface 43 attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough, and attenuates the X-rays so that the X-rays emitted from the X-ray tube 11 to the subject P exhibit predetermined distribution. For example, the wedge filter 16 (or bow-tie filter) is a filter obtained by processing aluminum so that it has a predetermined target angle and a predetermined thickness.

The collimator 17 is lead plates or the like for narrowing the application range of X-rays that have passed through the wedge filter 16, and includes a slit formed by combining the lead plates or the like. The collimator 17 may be referred to as an "X-ray diaphragm."

The DAS 18 generates digital data indicating counts of X-rays detected by the X-ray detector 12 (also referred to as "detection data") for each of a plurality of energy bands (referred to as "energy bins" or simply as "bins"). The detection data is a set of a channel number and row number of a source X-ray detection element, a view number indicating a collected view (also referred to as a projection angle), and data of the count value identified by the energy bin number. The DAS 18 is implemented by, for example, an application specific integrated circuit (ASIC) on which a circuit element capable of generating detection data is mounted. The detection data is transferred to the console 40.

The bed 30 is a device to place thereon the subject P to be scanned and move the subject P, and includes a base 31, a bed actuator 32, a table top 33, and a support frame 34.

The base 31 is a case that supports the support frame 34 movably in the vertical direction.

The bed actuator 32 is a motor or actuator that moves the table top 33 on which the subject P is placed in the longitudinal direction of the table top 33. The bed actuator 32 moves the table top 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the table top 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The table top 33 provided on the top surface of the support frame 34 is a plate on which the subject P is placed. The bed actuator 32 may move not only the table top 33 but the support frame 34 in the longitudinal direction of the table top 33.

The console 40 includes a memory 41, a display 42, an input interface 43, and processing circuitry 44. Data communication between the memory 41, the display 42, the input interface 43, and the processing circuitry 44 is performed via a bus. The console 40 is described as being separate from the gantry 10, but the gantry 10 may include the console 40 or part of each constituent element of the console 40.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but a driver that writes and reads various types of information in and from, for example, a portable storage medium such as CD, DVD, or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program according to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate. The display 42 may be provided in the gantry 10. The display 42 may either be a desktop type or configured by a tablet device capable of wirelessly communicating with the console 40.

The input interface 43 receives various types of input operations from the operator, converts a received input operation into an electrical signal, and outputs the electrical signal to the processing circuitry 44. For example, the input interface 43 receives, from the operator, a collection condition for collecting projection data, a reconstruction condition for reconstructing a CT image, and an image-processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44. The input interface 43 may be provided in the gantry 10. The input interface 43 may be configured by a tablet device capable of wirelessly communicating with the console 40.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, and a display control function 444. Each of the functions (the system control function 441, the pre-processing function 442, the reconstruction function 443, and the display control function 444) is not necessarily implemented by a single processing circuit. Processing circuitry can be configured by combining a plurality of independent processors, and the processors can execute respective programs to implement the functions.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43. For example, the system control function 441 obtains a two-dimensional positioning image of the subject P to determine the scan range, imaging condition, etc. The positioning image can also be referred to as a "scanogram" or "scout image."

The pre-processing function 442 generates data obtained by performing pre-processing on detection data output from the DAS 18, such as logarithmic conversion processing, offset correction processing, processing for sensitivity correction between channels, beam hardening correction, and correction for detector calibrations, detector nonlinearities, polar effects, noise balancing, and material decomposition. Data (detection data) before pre-processing and data after pre-processing can be collectively referred to as "projection data." The pre-processing function 442 is an example of the pre-processor.

The reconstruction function 443 generates CT image data by performing reconstruction processing using a filtered back projection method, a successive approximation reconstruction method, a stochastic image reconstruction method, or the like, on the projection data generated by the pre-processing function 442. The reconstruction function 443 is an example of the reconstruction processor. Image filtering, smoothing, volume rendering, or image differential processing can be applied to the CT image data if required. The display control function 444 converts CT image data generated by the reconstruction function 443 into tomographic image data of a given cross section, or three-dimensional image data by a publicly-known method, based on the input operation received from the operator via the input interface 43. The generation of three-dimensional image data can be performed directly by the reconstruction function 443. The display control function 444 is an example of the display controller.

In one implementation, the X-ray tube 11 is a single source emitting a broad spectrum of X-ray energies, and the PCD 12 can use a direct X-ray radiation detectors based on semiconductors, such as cadmium telluride (CdTe), cadmium zinc telluride (CZT), silicon (Si), mercuric iodide (HgI2), and gallium arsenide (GaAs). As mentioned above, semiconductor-based direct X-ray detectors generally have much faster time response than indirect detectors, such as scintillator detectors. The fast time response of direct detectors enables them to resolve individual X-ray detection events, although at the high X-ray fluxes typical in clinical X-ray applications, some pileup of detection events may occur. The energy of a detected X-ray is proportional to the signal generated by the direct detector, and the detection events can be organized into energy bins yielding spectrally resolved X-ray data for spectral CT.

Numerous modifications and variations of the embodiments presented herein are possible in light of the above teachings. It is therefore to be understood that within the scope of the claims, the application may be practiced otherwise than as specifically described herein. The inventions are not limited to the examples that have just been described; it is in particular possible to combine features of the illustrated examples with one another in variants that have not been illustrated.

Embodiments of the present disclosure may also be as set forth in the following parentheticals.

(1) A photon-counting imaging system, comprising: a photon-counting detector configured to acquire, from an imaging object, projection data for a plurality of projection views, the photon-counting detector having a plurality of detector pixels that are arranged in both a channel direction and a segment direction on a surface of the photon-counting detector; and processing circuitry configured to obtain the projection data acquired by the photon-counting detector, the projection data including first projection data and second projection data, process, with a first energy bin setting, the first projection data, the first energy bin setting indicating use of m energy bins, process, with a second energy bin setting, the second projection data, the second energy bin setting indicating use of n energy bins, where n>m, and generate, based on the processed first projection data and the processed second projection data, a material decomposition image of the imaging object.

(2) The system of (1), wherein the n energy bins are determined by a set of pre-defined energy thresholds of the photon-counting imaging system, and the m energy bins are determined by recombining the n energy bins in a pre-defined manner.

(3) The system of (1), wherein the photon-counting detector is further configured to: acquire the first projection data from detector pixels within a first area of the photon-counting detector, and acquire the second projection data from detector pixels within a second area of the photon-counting detector different from the first area.

(4) The system of (3), wherein the photon-counting detector is further configured to: acquire, from the detector pixels within the first area of the photon-counting detector, the first projection data from a first region of the imaging object where required image quality is lower than a predefined threshold, and acquire, from the detector pixels within the second area of the photon-counting detector, the second projection data from a second region of the imaging object where required image quality is equal to or higher than the predefined threshold.

(5) The system of (4), wherein the first area of the photon-counting detector corresponds to a peripheral portion of the photon-counting detector in at least one of the channel direction and the segment direction, and the second area of the photon-counting detector corresponds to a central portion of the photon-counting detector in the at least one of the channel direction and the segment direction.

(6) The system of (3), wherein the first area of the photon-counting detector and the second area of the photon-counting detector are located on the surface of the photon-counting detector side by side in at least one of the channel direction and the segment direction.

(7) The system of (3), wherein a transition zone is arranged around a boundary between the first area and the second area of the photon-counting detector, and the processing circuitry is further configured to process, with both the first energy bin setting and the second energy bin setting, projection data acquired by detector pixels within the transition zone.

(8) The system of (3), wherein the first area of the photon-counting detector includes k subareas, detector pixels within each of the k subareas acquiring one of k subsets of the first projection data, and the processing circuitry is further configured to process, with k energy bin subsettings, the k subsets of the first projection data, respectively, wherein for $1 \leq i \leq k$, an i-th energy bin subsetting indicates use of $m_i$ energy bins, and $m_i < n$.

(9) The system of (8), wherein for $1 \leq j \leq k-1$, a transition zone is arranged around a boundary between a j-th subarea and a (j+1)-th subarea of the photon-counting detector, and the processing circuitry is further configured to process, with both a j-th energy bin subsetting and a (j+1)-th energy bin subsetting, projection data acquired by detector pixels within the transition zone between the j-th subarea and the (j+1)-th subarea.

(10) The system of (3), wherein the processing circuitry is further configured to process, with a predefined group of p energy bin subsettings, the first projection data, in a channel-based, segment-based, or view-based manner.

(11) The system of (10), wherein the processing circuitry is further configured to process, with an x-th energy bin subsetting of the predefined group, projection data acquired by an x-th pixel channel of each p consecutive pixel channels within the first area, where $1 \leq x \leq p$.

(12) The system of (10), wherein the processing circuitry is further configured to process, with an x-th energy bin subsetting of the predefined group, projection data acquired by an x-th pixel segment of each p consecutive pixel segments within the first area, where $1 \leq x \leq p$.

(13) The system of (10), wherein the processing circuitry is further configured to process, with an x-th energy bin subsetting of the predefined group, the first projection data acquired for an x-th projection view of each p consecutive projection views, where $1 \leq x \leq p$.

(14) The system of (1), wherein the photon-counting detector is further configured to: acquire the first projection data for a first subset of the plurality of projection views, and acquire the second projection data for a second subset of the plurality of projection views.

(15) The system of (14), wherein the first subset of the plurality of projection views includes even-numbered projection views, while the second subset of projection views includes odd-numbered projection views, or the first subset of the plurality of projection views includes odd-numbered projection views, while the second subset of projection views includes even-numbered projection views.

(16) A method for performing pixel-based energy bin number modulation in a photon-counting imaging system, the photon-counting imaging system including a photon-counting detector that acquires, from an imaging object, projection data for a plurality of projection views, the photon-counting detector having a plurality of detector pixels that are arranged in both a channel direction and a segment direction on a surface of the photon-counting detector, the method comprising: obtaining the projection data acquired by the photon-counting detector, the projection data including first projection data and second projection data; processing, with a first energy bin setting, the first projection data, the first energy bin setting indicating use of m energy bins; processing, with a second energy bin setting, the second projection data, the second energy bin setting indicating use of n energy bins, where n>m; and generating, based on the processed first projection data and the processed second projection data, a material decomposition image of the imaging object.

(17) The method of (16), wherein the n energy bins are determined by a set of pre-defined energy thresholds of the photon-counting imaging system, and the m energy bins are determined by recombining the n energy bins in a pre-defined manner.

(18) The method of (16), wherein the obtaining step further comprises: acquiring the first projection data from detector pixels within a first area of the photon-counting detector, and acquiring the second projection data from detector pixels within a second area of the photon-counting detector.

(19) The method of (16), wherein the obtaining step further comprises: acquiring the first projection data for a first subset of the plurality of projection views, and acquiring the second projection data for a second subset of the plurality of projection views.

(20) A non-transitory computer-readable medium storing a program that, when executed by processing circuitry, causes the processing circuitry to execute a method for performing pixel-based energy bin number modulation in a photon-counting imaging system, the photon-counting imaging system including a photon-counting detector that acquires, from an imaging object, projection data for a plurality of projection views, the photon-counting detector having a plurality of detector pixels that are arranged in both a channel direction and a segment direction on a surface of the photon-counting detector, the method comprising: obtaining the projection data acquired by the photon-counting detector, the projection data including first projection data and second projection data; processing, with a first energy bin setting, the first projection data, the first energy bin setting indicating use of m energy bins; processing, with a second energy bin setting, the second projection data, the second energy bin setting indicating use of n energy bins, where n>m; and generating, based on the processed first projection data and the processed second projection data, a material decomposition image of the imaging object.

Numerous modifications and variations of the embodiments presented herein are possible in light of the above teachings. It is therefore to be understood that within the scope of the claims, the disclosure may be practiced otherwise than as specifically described herein.

The invention claimed is:

1. A photon-counting imaging system, comprising:
a photon-counting detector configured to acquire, from an imaging object, projection data for a plurality of projection views, the photon-counting detector having a plurality of detector pixels that are arranged in both a channel direction and a segment direction on a surface of the photon-counting detector; and
processing circuitry configured to
obtain the projection data acquired by the photon-counting detector, the projection data including first projection data and second projection data, the first projection data being acquired by detector pixels different from detector pixels that acquired the second projection data,
process, with a first energy bin setting, the first projection data, the first energy bin setting indicating use of m energy bins,
process, with a second energy bin setting, the second projection data, the second energy bin setting indicating use of n energy bins, where n>m, and
generate, based on the processed first projection data and the processed second projection data, a material decomposition image of the imaging object.

2. The system of claim 1, wherein
the n energy bins are determined by a set of pre-defined energy thresholds of the photon-counting imaging system, and
the m energy bins are determined by recombining the n energy bins in a pre-defined manner.

3. The system of claim 1, wherein the photon-counting detector is further configured to:
acquire the first projection data from detector pixels within a first area of the photon-counting detector, and
acquire the second projection data from detector pixels within a second area of the photon-counting detector different from the first area.

4. The system of claim 3, wherein the photon-counting detector is further configured to:
acquire, from the detector pixels within the first area of the photon-counting detector, the first projection data from a first region of the imaging object where required image quality is lower than a predefined threshold, and
acquire, from the detector pixels within the second area of the photon-counting detector, the second projection data from a second region of the imaging object where required image quality is equal to or higher than the predefined threshold.

5. The system of claim 4, wherein
the first area of the photon-counting detector corresponds to a peripheral portion of the photon-counting detector in at least one of the channel direction and the segment direction, and the second area of the photon-counting detector corresponds to a central portion of the photon-counting detector in the at least one of the channel direction and the segment direction.

6. The system of claim 3, wherein the first area of the photon-counting detector and the second area of the photon-counting detector are located on the surface of the photon-counting detector side by side in at least one of the channel direction and the segment direction.

7. The system of claim 3, wherein a transition zone is arranged around a boundary between the first area and the second area of the photon-counting detector, and
the processing circuitry is further configured to process, with both the first energy bin setting and the second energy bin setting, projection data acquired by detector pixels within the transition zone.

8. The system of claim 3, wherein
the first area of the photon-counting detector includes k subareas, detector pixels within each of the k subareas acquiring one of k subsets of the first projection data, and
the processing circuitry is further configured to process, with k energy bin subsettings, the k subsets of the first projection data, respectively, wherein for $1 \leq i \leq k$, an i-th energy bin subsetting indicates use of $m_i$ energy bins, and $m_i < n$.

9. The system of claim 8, wherein
for $1 \leq j \leq k-1$, a transition zone is arranged around a boundary between a j-th subarea and a (j+1)-th subarea of the photon-counting detector, and
the processing circuitry is further configured to process, with both a j-th energy bin subsetting and a (j+1)-th energy bin subsetting, projection data acquired by detector pixels within the transition zone between the j-th subarea and the (j+1)-th subarea.

10. The system of claim 3, wherein the processing circuitry is further configured to:
process, with a predefined group of p energy bin subsettings, the first projection data, in a channel-based, segment-based, or view-based manner.

11. The system of claim 10, wherein the processing circuitry is further configured to:
process, with an x-th energy bin subsetting of the predefined group, projection data acquired by an x-th pixel channel of each p consecutive pixel channels within the first area, where $1 \leq x \leq p$.

12. The system of claim 10, wherein the processing circuitry is further configured to:
process, with an x-th energy bin subsetting of the predefined group, projection data acquired by an x-th pixel segment of each p consecutive pixel segments within the first area, where $1 \leq x \leq p$.

13. The system of claim 10, wherein the processing circuitry is further configured to:
process, with an x-th energy bin subsetting of the predefined group, the first projection data acquired for an x-th projection view of each p consecutive projection views, where $1 \leq x \leq p$.

14. The system of claim 1, wherein the photon-counting detector is further configured to:
acquire the first projection data for a first subset of the plurality of projection views, and
acquire the second projection data for a second subset of the plurality of projection views.

19 20

15. The system of claim 14, wherein
the first subset of the plurality of projection views includes even-numbered projection views, while the second subset of projection views includes odd-numbered projection views, or
the first subset of the plurality of projection views includes odd-numbered projection views, while the second subset of projection views includes even-numbered projection views.

16. A method for performing pixel-based energy bin number modulation in a photon-counting imaging system, the photon-counting imaging system including a photon-counting detector that acquires, from an imaging object, projection data for a plurality of projection views, the photon-counting detector having a plurality of detector pixels that are arranged in both a channel direction and a segment direction on a surface of the photon-counting detector, the method comprising:
obtaining the projection data acquired by the photon-counting detector, the projection data including first projection data and second projection data, the first projection data being acquired by detector pixels different from detector pixels that acquired the second projection data;
processing, with a first energy bin setting, the first projection data, the first energy bin setting indicating use of m energy bins;
processing, with a second energy bin setting, the second projection data, the second energy bin setting indicating use of n energy bins, where n>m; and
generating, based on the processed first projection data and the processed second projection data, a material decomposition image of the imaging object.

17. The method of claim 16, wherein
the n energy bins are determined by a set of pre-defined energy thresholds of the photon-counting imaging system, and
the m energy bins are determined by recombining the n energy bins in a pre-defined manner.

18. The method of claim 16, wherein the obtaining step further comprises:
acquiring the first projection data from detector pixels within a first area of the photon-counting detector, and
acquiring the second projection data from detector pixels within a second area of the photon-counting detector.

19. The method of claim 16, wherein the obtaining step further comprises:
acquiring the first projection data for a first subset of the plurality of projection views, and
acquiring the second projection data for a second subset of the plurality of projection views.

20. A non-transitory computer-readable medium storing a program that, when executed by processing circuitry, causes the processing circuitry to execute a method for performing pixel-based energy bin number modulation in a photon-counting imaging system, the photon-counting imaging system including a photon-counting detector that acquires, from an imaging object, projection data for a plurality of projection views, the photon-counting detector having a plurality of detector pixels that are arranged in both a channel direction and a segment direction on a surface of the photon-counting detector, the method comprising:
obtaining the projection data acquired by the photon-counting detector, the projection data including first projection data and second projection data, the first projection data being acquired by detector pixels different from detector pixels that acquired the second projection data;
processing, with a first energy bin setting, the first projection data, the first energy bin setting indicating use of m energy bins;
processing, with a second energy bin setting, the second projection data, the second energy bin setting indicating use of n energy bins, where n>m; and
generating, based on the processed first projection data and the processed second projection data, a material decomposition image of the imaging object.

* * * * *